US011903814B2

(12) United States Patent
Graf et al.

(10) Patent No.: US 11,903,814 B2
(45) Date of Patent: Feb. 20, 2024

(54) DELIVERY SLEEVE

(71) Applicant: MENTOR WORLDWIDE LLC, Irvine, CA (US)

(72) Inventors: Udo Werner Graf, Goleta, CA (US); Joseph Matton, Irvine, CA (US); Leo Kriksunov, Ithaca, NY (US); Robert Tannhauser, Bridgewater, NJ (US)

(73) Assignee: MENTOR WORLDWIDE LLC, Irvine, CA (US)

( * ) Notice: Subject to any disclaimer, the term of this patent is extended or adjusted under 35 U.S.C. 154(b) by 1016 days.

(21) Appl. No.: 15/913,484

(22) Filed: Mar. 6, 2018

(65) Prior Publication Data
US 2019/0274819 A1   Sep. 12, 2019

(51) Int. Cl.
*A61F 2/12* (2006.01)
*A61F 2/00* (2006.01)
*A61B 17/34* (2006.01)
*A61B 17/00* (2006.01)

(52) U.S. Cl.
CPC .............. *A61F 2/12* (2013.01); *A61F 2/0095* (2013.01); *A61B 17/3468* (2013.01); *A61B 2017/00792* (2013.01)

(58) Field of Classification Search
CPC ....................................................... A61F 2/12
See application file for complete search history.

(56) References Cited

U.S. PATENT DOCUMENTS

| 4,035,850 A | 7/1977 | Cresswall |
| 4,955,906 A | 9/1990 | Coggins et al. |
| 5,201,779 A | 4/1993 | Shiao |
| 5,279,539 A * | 1/1994 | Bohan .............. A61B 17/00234 600/37 |

(Continued)

FOREIGN PATENT DOCUMENTS

| CN | 2897165 Y | 5/2007 |
| CN | 208552129 U | 3/2019 |

(Continued)

OTHER PUBLICATIONS

PCT Notification of Transmittal of the International Search Report and International Search Report of International Application No. PCT/IB2019/051820 dated Jun. 18, 2019, 8 pages.

(Continued)

*Primary Examiner* — Jerrah Edwards
*Assistant Examiner* — Christine L Nelson
(74) *Attorney, Agent, or Firm* — Etan S. Chatlynne; Calderon Safran & Cole P.C.

(57) ABSTRACT

A delivery sleeve for assisting delivery of a tissue implant may include an enclosure an orifice, and a throat. A cinching mechanism, which may include a fastener, may be disposed about the throat. The fastener may be used to fasten the cinching mechanism in a cinched configuration to maintain the throat in a closed configuration. The cinching mechanism may include implant-size indicators thereon. A lubricant or lubricious material may be included upon an inner surface of the enclosure. The cinching mechanism may be (Continued)

used to change the configuration of the throat from an open configuration to a closed configuration. The fastener helps maintain the throat in a closed configuration.

15 Claims, 7 Drawing Sheets

(56) References Cited

U.S. PATENT DOCUMENTS

| | | | |
|---|---|---|---|
| 5,549,679 A * | 8/1996 | Kuslich | A61F 2/4611 623/17.12 |
| 5,723,006 A | 3/1998 | Ledergerber | |
| 5,728,065 A | 3/1998 | Follmer et al. | |
| 6,467,612 B1 | 10/2002 | Rosenfeld | |
| 6,605,093 B1 | 8/2003 | Blake | |
| 8,070,768 B2 | 12/2011 | Kim et al. | |
| 8,182,459 B2 | 5/2012 | Dann et al. | |
| 8,187,297 B2 | 5/2012 | Makower et al. | |
| 8,211,173 B2 | 7/2012 | Keller et al. | |
| 8,409,279 B2 | 4/2013 | Freund | |
| 8,641,758 B1 | 2/2014 | Anderson et al. | |
| 8,993,831 B2 | 3/2015 | Sharma et al. | |
| 9,414,941 B2 | 8/2016 | Placik et al. | |
| 10,105,213 B2 | 10/2018 | Weinzweig | |
| 10,842,602 B2 | 11/2020 | Alexander et al. | |
| 11,324,581 B2 | 5/2022 | Heneveld | |
| 11,452,511 B2 | 9/2022 | Barbot et al. | |
| 11,690,614 B2 | 7/2023 | Gross et al. | |
| 11,690,716 B2 | 7/2023 | Hosmer et al. | |
| 11,712,345 B2 | 8/2023 | Olmos et al. | |
| 11,723,769 B2 | 8/2023 | Basude et al. | |
| 2002/0091443 A1 | 7/2002 | Yoon | |
| 2004/0225278 A1 | 11/2004 | Poole et al. | |
| 2005/0080430 A1 | 4/2005 | Wright et al. | |
| 2007/0276484 A1 | 11/2007 | Abell et al. | |
| 2008/0167606 A1 | 7/2008 | Dann et al. | |
| 2009/0030400 A1 | 1/2009 | Bose et al. | |
| 2009/0204107 A1 | 8/2009 | Keller et al. | |
| 2011/0082546 A1 * | 4/2011 | Freund | A61F 2/12 623/8 |
| 2011/0144688 A1 | 6/2011 | Reiss et al. | |
| 2014/0148901 A1 | 5/2014 | Anderson et al. | |
| 2014/0228951 A1 * | 8/2014 | Zochowski | A61F 2/12 623/8 |
| 2014/0249510 A1 | 9/2014 | Koblish et al. | |
| 2014/0350462 A1 | 11/2014 | Ataollahi et al. | |
| 2015/0032208 A1 | 1/2015 | Preissman | |
| 2016/0095733 A1 | 4/2016 | Sharma et al. | |
| 2016/0374720 A1 | 12/2016 | Anderson et al. | |
| 2017/0007295 A1 | 1/2017 | Geisz | |
| 2017/0020500 A1 | 1/2017 | Taylor et al. | |
| 2017/0303905 A1 | 10/2017 | Wilson | |
| 2018/0116779 A1 | 5/2018 | Marx | |
| 2018/0126119 A1 | 5/2018 | McNiven et al. | |
| 2019/0274817 A1 | 9/2019 | Hristov et al. | |
| 2019/0274818 A1 | 9/2019 | Hristov et al. | |
| 2019/0343620 A1 | 11/2019 | Mlodinow et al. | |
| 2020/0222174 A1 | 7/2020 | Rosenberg | |
| 2021/0052359 A1 | 2/2021 | Heneveld | |
| 2021/0244527 A1 | 8/2021 | Heneveld | |
| 2022/0000604 A1 | 1/2022 | Graf et al. | |
| 2022/0054254 A1 | 2/2022 | Gryskiewicz et al. | |
| 2022/0233297 A1 | 7/2022 | Heneveld | |
| 2022/0241066 A1 | 8/2022 | Hristov et al. | |
| 2023/0060747 A1 | 3/2023 | Marks et al. | |
| 2023/0098318 A1 | 3/2023 | Hristov et al. | |
| 2023/0255608 A1 | 8/2023 | Sarna et al. | |

FOREIGN PATENT DOCUMENTS

| | | |
|---|---|---|
| EP | 2 630 927 A2 | 8/2013 |
| WO | 2010/099541 A1 | 9/2010 |
| WO | 2010/126462 A1 | 11/2010 |
| WO | 2012177587 A1 | 12/2012 |
| WO | 2017/213716 A1 | 12/2017 |
| WO | 2019/171300 A1 | 9/2019 |

OTHER PUBLICATIONS

Shaa'ista Ameen, 'No-Touch' Breast-Implant Insertion Device, Submitted to the University of Cape Town, Faculty of Health Sciences, Department of Human Biology, University of Cape Town, Date of Submission: Jan. 1, 2016, URL: https://open.uct.ac.za/bitstream/handle/11427/20491/thesis_hsf_2016_ameen_shaa_039_ista.pdf?sequene=1 [retrieved on Feb. 27, 2018], pp. 74-76.

PCT Notification of Transmittal of the International Search Report and the Written Opinion of the International Searching Authority, or the Declaration for International Application No. PCT/IB2021/055927 dated Oct. 4, 2021, 6 pages.

* cited by examiner

DELIVERY SLEEVE

CROSS-REFERENCE TO CO-PENDING APPLICATIONS

This application is a counterpart of U.S. patent application Ser. No. 15/913,438, filed Mar. 6, 2018, and Ser. No. 15/913,463, filed Mar. 6, 2018, which are incorporated by reference herein in their entirety.

FIELD

The subject matter disclosed herein relates to devices and methods for delivering implants into a subject.

BACKGROUND

Tapered flexible sleeves, such as that marketed under the brand name, KELLER FUNNEL®, may be used as a delivery device for implanting a tissue implant, such as a silicone-gel breast implant, into a subject. These sleeves permit delivery of the implant through an incision that is shorter than it would need to be if the sleeve were not used. These sleeves may also lower the likelihood of introducing contaminants, e.g., microorganisms, into the subject through the incision because they minimize the amount of contact between the implant, surgeon's hands, and subject's tissue.

SUMMARY

Disclosed herein is a delivery sleeve that may be used to deliver an implant, e.g., a tissue implant such as a breast implant, particularly of the silicone-gel variety. The delivery sleeve may include an enclosure having a bulbous portion, an orifice, and a throat disposed between the bulbous portion and the orifice. In certain embodiments, the orifice may be a single orifice. In other embodiments, one or more additional orifices may be included. A tissue implant may be disposed within the enclosure. A cinching mechanism may be disposed about the throat. The cinching mechanism may include a fastener. The fastener may be used to fasten the cinching mechanism in a cinched configuration to maintain the throat in a closed configuration. The cinching mechanism may include a string, filament, tape, strap, band, cable tie, ribbon, or a combination thereof. The fastener may include a hook-and-loop fastener, a cord lock, a ratchet, an elastic ring, a magnetic ring, or a combination thereof. The fastener may be a releasable fastener. Further, an eyelet may be disposed on the throat and a portion of the cinching mechanism may be disposed through the eyelet. Additionally, the cinching mechanism may include sizing indicators thereon. For example, the sizing indicators may denote sizes of various implants. Thus, the cinching mechanism may include implant-size indicators thereon. A lubricant or lubricious material may be included upon an inner surface of the enclosure.

In some embodiments, the delivery sleeve may include an enclosure having a throat with an orifice, which may be a single orifice, and a cinching mechanism having a fastener. The cinching mechanism may be disposed about the throat in a cinched configuration such that the throat and the orifice are in a closed configuration. The enclosure may have a bulbous form or it may have a tapered form. The throat may have a cylindrical shape. Alternatively, the throat may have a conical shape. Further, the cinching mechanism may include implant-size indicators thereon. A tissue implant may be disposed within the enclosure.

The delivery sleeve may be used according to the following methods and variations. A tissue implant may be provided and the delivery sleeve may be provided. The delivery sleeve may be provided with the cinching mechanism disposed about the throat in a loose configuration such that the throat and the orifice are in an open configuration. The tissue implant may be inserted into the enclosure through the orifice and the throat. The configuration of the throat may be changed from the open configuration to a closed configuration by cinching the cinching mechanism into a cinched configuration. In some variations, the throat has a cylindrical shape in the closed configuration. In other variations, the throat has a conical shape in the closed configuration. The delivery sleeve may be used to assist delivering the tissue implant into a tissue pocket of a subject, e.g., a human female patient. Accordingly, the orifice in the closed configuration may be inserted through an incision upon the subject.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

DETAILED DESCRIPTION

The following description sets forth certain illustrative examples of the claimed subject matter. Other examples, features, aspects, embodiments, and advantages of the technology should become apparent to those skilled in the art from the following description. Accordingly, the drawings and descriptions should be regarded as illustrative in nature.

Figure 1:
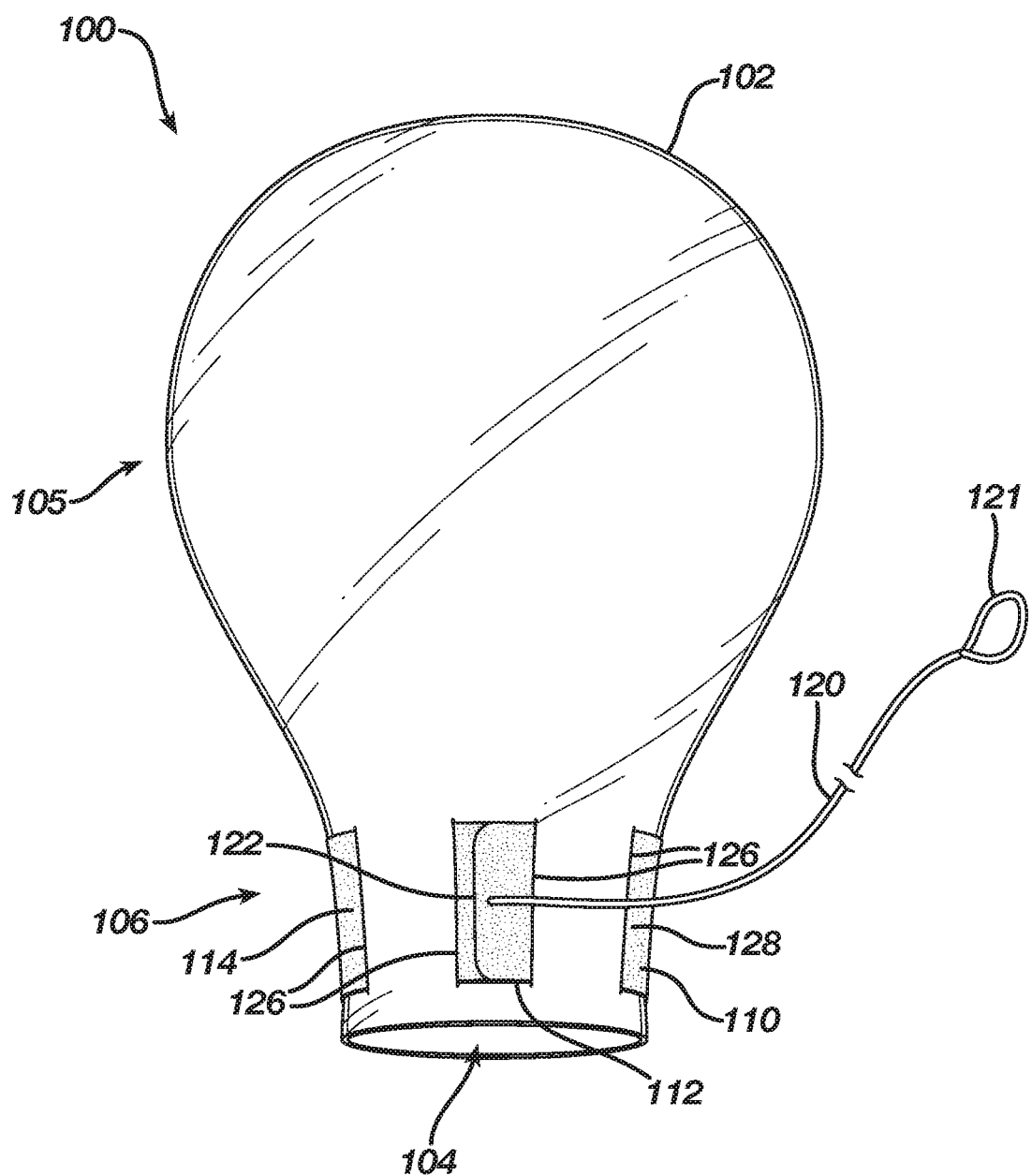
FIG. 1 depicts a delivery sleeve.
Figure 2:
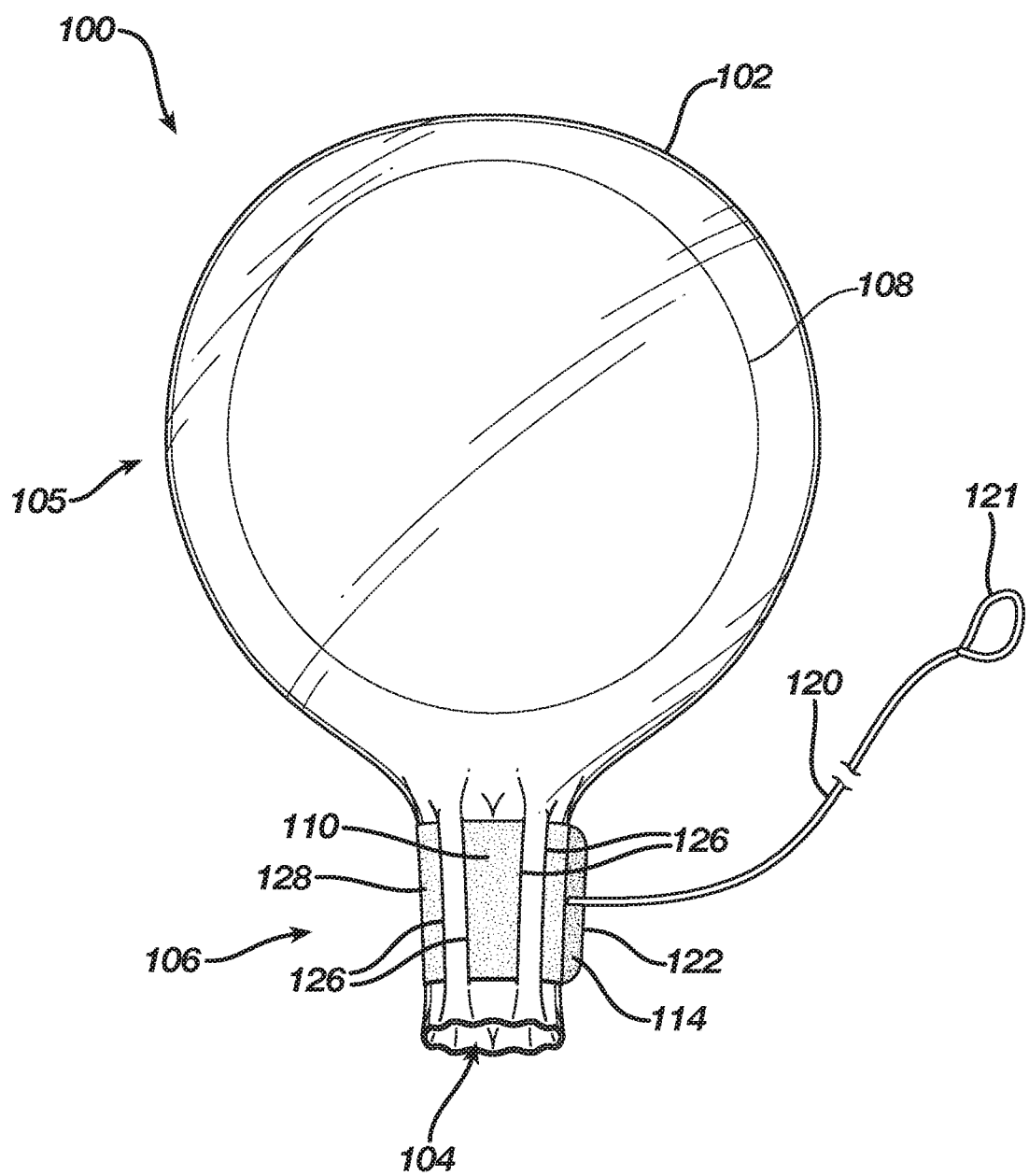
FIG. 2 depicts the delivery sleeve of FIG. 1 in a closed configuration.

FIGS. 1 and 2 show an exemplary embodiment of a delivery sleeve 100. Delivery sleeve 100 may include a thin-walled enclosure 102 with an orifice 104, a bulbous portion 105, and a throat or throat portion 106 connecting bulbous portion 105 to orifice 104. In some embodiments, orifice 104 is disposed at an end of throat 106 and may be considered a portion of throat 106. As reflected in FIG. 2, an implant 108, e.g., a silicone-gel implant, may be provided within enclosure 102, typically within bulbous portion 105. Enclosure 102 may be fabricated by any suitable process, e.g., blow molding or sealing two sheets of a suitable material, e.g., vinyl, together to form a seal. In some embodiments, throat 106 and orifice 104 each have a diameter or width that is less than a diameter or width of the other portion(s) of enclosure 102, i.e., bulbous portion 105.

Implant 108 may be a breast implant or another type of implant (e.g., biopsy, lumpectomy, calf, buttock, or pectoral). Breast implants typically have a maximum diameter or maximum width ranging from between approximately three inches and eight inches. Implants may be referred to by their maximum width or diameter taken in a plane that is parallel to the base of the implant, e.g., "a five-inch implant." Silicone-gel implants are flexible and pliable, and may be squeezed considerably to constrain the implant in a configuration such that the diameter of the implant may be constricted considerably, e.g., on the order of between approximately two to ten times. For example, if implant 106 is a "three-inch implant" the portion that is three inches may be squeezed to constrict that portion down to a width of, e.g., 1.5 inches. Once the constrictive forces are removed, the portion recovers its original shape having a three-inch diameter.

Bulbous portion 105 may be designed to conform, loosely conform, or loosely surround implant 108, depending on the size. For example, a delivery sleeve 100 may be designed as a delivery sleeve for most or all implant sizes. So designed, bulbous portion 105 may have a maximum width or diameter of between approximately six to eight inches. For example, the maximum width or diameter of bulbous portion 105 may be approximately eight inches. Alternatively, delivery sleeve 100 may be designed as a delivery sleeve for a range of implant sizes, e.g. three- to five-inch implants. In such instances, bulbous portion 105 may have a width or diameter between approximately four to six inches. For example, bulbous portion 105 may have a width or diameter of approximately five inches. Of course, bulbous portion 105 may be provided with smaller diameters, e.g., between approximately one inch and three inches, for other types of and smaller sized implants or with larger diameters, e.g., between approximately eight inches and ten inches, for other types of and larger sized implants. Other types of implants include lumpectomy, biopsy, calf, buttocks, pectoral, etc.

Throat 106 may have a maximum width or diameter that is less than or equal to the width or diameter of bulbous portion 105. As shown in FIG. 1, throat 106 is somewhat narrower than bulbous portion 105. In some embodiments, the diameter or width of throat 106 is at least approximately equal to the maximum diameter or width of implant 108, e.g., between approximately three inches and eight inches. Such dimensions may facilitate introducing implant 108 into enclosure 102 because implant 108 need not be compressed and throat 106 need not be stretched to remove interference caused by the throat being narrower than the implant.

The diameter or width of throat 106 is adjustable. A cinching mechanism 110 may be disposed about throat 106, which may be used to adjust the diameter or width of throat 106. In various embodiments, a cinching mechanism may include a string, filament, tape, strap, band, cable tie, or ribbon, or a combination thereof. In various embodiments, the cinching mechanism may include at least a single band or string, and/or multiple bands or strings. In various embodiments the cinching mechanism may also include a fastener, such as a hook-and-loop type fastener (e.g., VELCRO®), a cord lock (which may be spring loaded), a ratchet (e.g., as in the teeth and pawl of a zip-type cable tie), an elastic ring, or a magnetic ring. The fastener may be used to restrain cinching mechanism 110 in a desired configuration.

As reflected in FIGS. 1 and 2, cinching mechanism 110 comprises a band or cable tie 128 disposed about throat 106 and having a hook-and-loop type fastener 114. In some embodiments, cinching mechanism 110 may also comprise a pull cord 120, which may have a loop 121 for a user to pull, connected to an end 122 of band 128. Further, in some embodiments, slits, e.g., slits 126 may be disposed through throat 106 and band 128 disposed therethrough such that band 128 may be woven through the slits, akin to a purse string. Alternatively, instead of slits, a sleeve may be disposed about and attached circumferentially to throat 106 such that band 128 may be disposed through the sleeve and about throat 106. Alternatively, instead of a sleeve, a channel may be formed about and circumferentially on throat 106 such that band 128 may be disposed through the channel and about throat 106. Alternatively, eyelets may be affixed circumferentially to throat 106 such that band 128 may be disposed through the eyelets and about throat 106.

An edge 112 of band 128 may be disposed about orifice 104 or may be spaced from orifice 104 by between approximately 0.1 inches and 2 inches. For example, the distance between orifice 104 and edge 112 may be approximately 0.5 inches. In FIG. 1, cinching mechanism 110 is shown in a loose configuration such that orifice 104 is in an open configuration. However, in FIG. 2, cinching mechanism 110 is shown in a cinched configuration such that throat 106 and orifice 104 are in a closed configuration. The hook-and-loop fastener 114 is fastened such that cinching mechanism 110 is maintained in the cinched configuration and throat 106 and orifice 104 are maintained in the closed configuration.

In FIG. 2, throat 106 and orifice 104 are maintained in a closed configuration such that throat 106 has a cylindrical or approximately cylindrical shape. Notably, the diameter or width of throat 106 is substantially less than it was in the open configuration of FIG. 1, and it is also substantially less than the diameter or width of bulbous portion 105, which contains implant 108. Thus, throat 106 and orifice 104 may have a width or diameter that approximates a width of an incision through which implant 108 is to be inserted into a subject. Alternatively, the width or diameter of throat 106 and orifice 104 in the closed configuration may be between approximately one quarter to three quarters of the maximum width or diameter of implant 108. Because breast implants typically have a maximum width or diameter between approximately three inches and eight inches, throat 106 may have a width or diameter in the closed configuration between approximately 0.75 inches (i.e., one quarter of three inches) and six inches (i.e., three quarters of eight inches). For example, if implant 108 is a five-inch implant, the width or diameter of throat 106 in the closed configuration may be between approximately 1.2 inches and 3.8 inches. Although the width or diameter of throat 106 in the closed configuration has been provided based upon typical breast-implant sizes, it should be understood that delivery sleeve 100 may be used to deliver other types of implants (e.g., lumpectomy, biopsy, calf, buttocks and pectoral implants). Accordingly, the width or diameter of throat 106 in the closed configuration may also be between approximately 0.2 inches and 0.8 inches or between approximately six inches and eight inches. In some embodiments, band 128 may include graphical representations, e.g., indicators or markings that are symbolic or numeric, indicating the size of orifice 104 and/or throat 106 in the closed configuration, or the size of the implant to be introduced. Because throat 106 may have a diameter or width in the closed configuration that is less than a width of an incision through which implant 108 will pass, such incisions typically ranging from approximately two inches to approximately five inches, opening 104 and a portion of throat 106 may be inserted through the incision with relative ease, minimal trauma, and minimal contact with tissues surrounding the incision.

A manufacturer of sleeve 100 may provide a sterilized and packaged product that includes enclosure 102 with implant 108 disposed therein. For example, the manufacturer may insert implant 108 into enclosure 102 through orifice 104 and throat 106 while they are in an open configuration, and then cinch cinching mechanism 110 and fasten fastener 114 to change the configuration of orifice 104 and throat 106 to a closed configuration. Alternatively, a manufacturer of sleeve 100 may provide a sterilized and packaged product that includes enclosure 102 but excludes implant 108 such that a medical professional, e.g., surgeon, would provide implant 108 and insert implant 108 into enclosure 102 through orifice 104 and throat 106, and then cinch cinching mechanism 110 herself.

After implant 108 is disposed within enclosure 102 and after cinching mechanism 110 has been cinched to place throat 106 and orifice 104 into the closed configuration, orifice 104 and a portion of throat 106 may be passed through an incision and into a tissue pocket, e.g., a breast pocket, of a subject, such as a human female patient. Once the medical professional has positioned orifice 104 at a desired location, she may squeeze enclosure 102 about implant 108 to force or extrude implant 108 through throat 106 and out of orifice 104 into the tissue pocket. The medical professional may then remove throat 106 and orifice 104 from the tissue pocket through the incision, leaving implant 108 behind. In some variations, before forcing or extruding the implant through throat 106, the medical professional may release fastener 114, e.g., by pulling on end 122. In those embodiments that include pull cord 120, this action may be facilitated by pulling on pull cord 120, e.g., by pulling on loop 121. Once unfastened, such that cinching mechanism 110 is no longer in the cinched configuration, and throat 106 and orifice 104 are no longer constrained in the closed configuration, implant 108 may be passed into the tissue pocket, through throat 106 and orifice 104, by squeezing enclosure 102, perhaps with less force than if throat 106 remained in the cinched configuration. Either way, after implant 108 is disposed in the tissue pocket, the medical professional may remove throat 106 and orifice 104 from the tissue pocket through the incision, leaving implant 108 behind.

As shown, orifice 104 is a single orifice, however, in some embodiments, additional orifices may be included elsewhere on enclosure 102. In some embodiments (not shown) a second orifice may be included opposite orifice 104. This second orifice may be sized to permit insertion of implant 108 into enclosure 102, e.g., without deforming implant 108. In some embodiments (not shown), enclosure 102 may not have the bulbous form reflected in the figures. Rather, it may have a tapered (e.g., frustoconical) form. In these tapered embodiments, the width of enclosure 102 is largest at the end opposite orifice 104 and is smallest at the end including opening 104.

Figure 3:
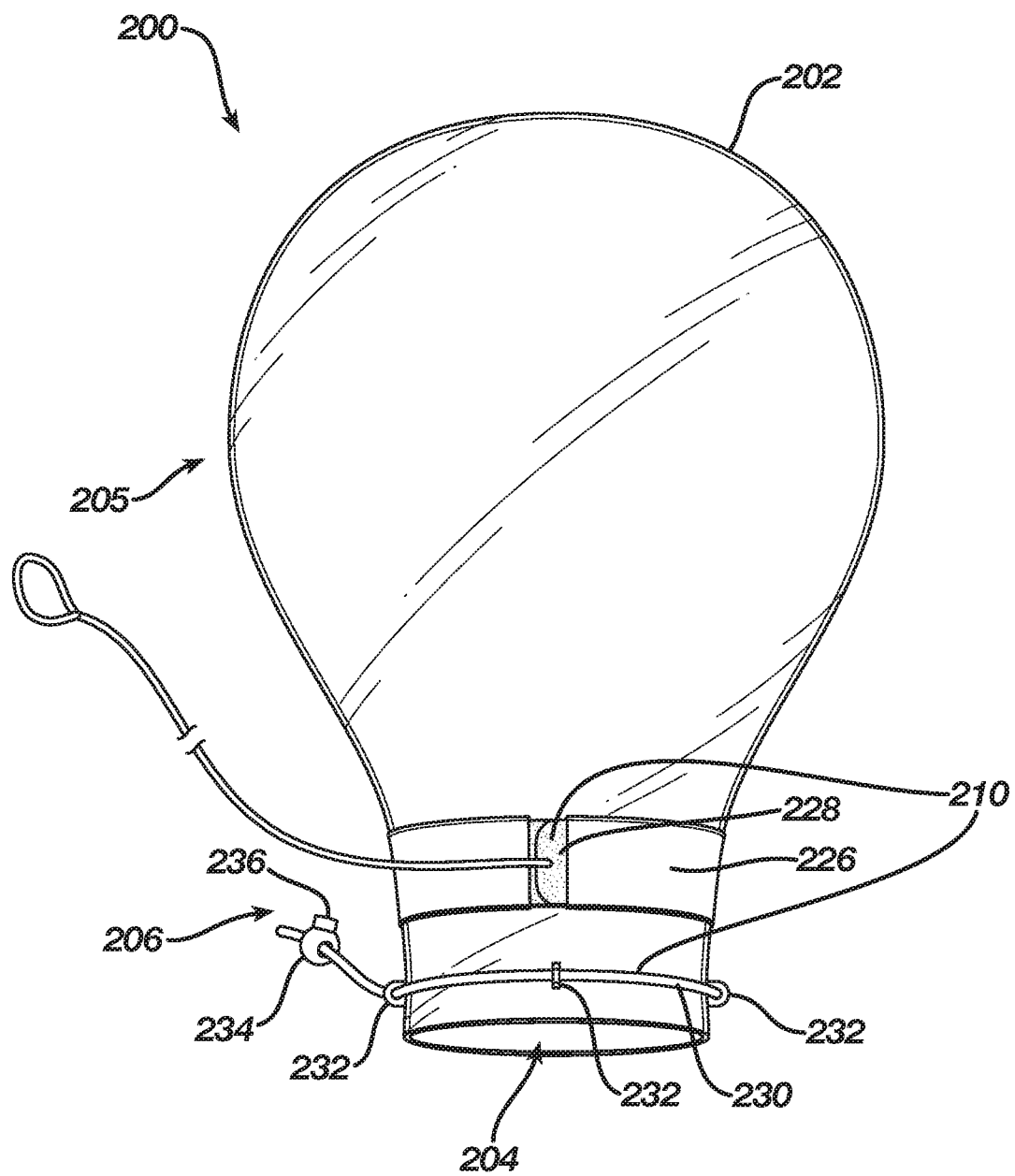
FIG. 3 depicts a first alternate embodiment of a delivery sleeve.
Figure 4:
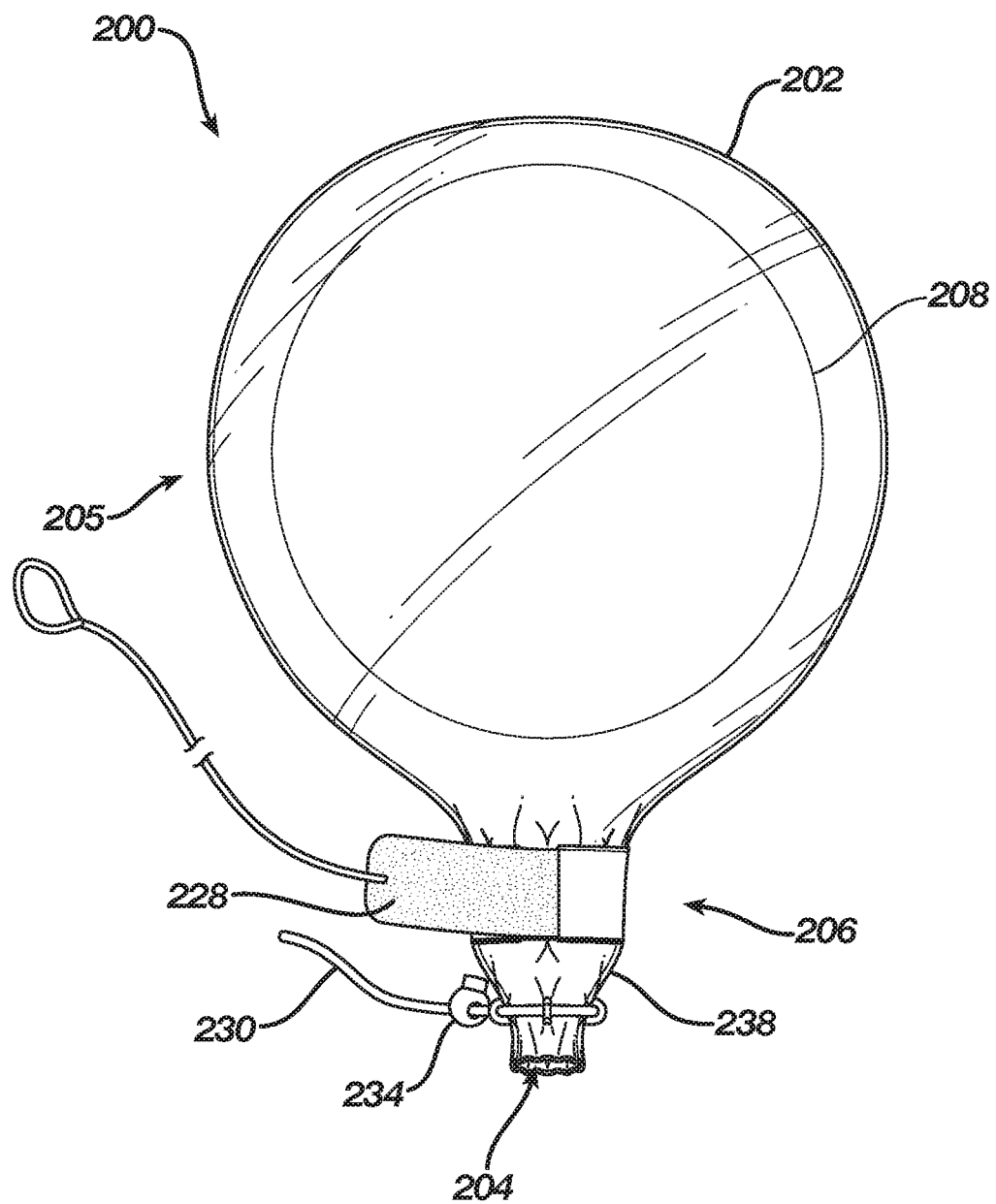
FIG. 4 depicts the delivery sleeve of FIG. 3 in a closed configuration.

FIGS. 3 and 4 show an alternate embodiment of a delivery sleeve. Delivery sleeve 200 includes an enclosure 202 comprising a cinching mechanism 210 that includes a band 228 disposed about throat 206 through a sleeve 226 that is disposed circumferentially around throat 206, adjacent to bulbous portion 205. Cinching mechanism 210 also includes a string 230 disposed about orifice 204 through eyelets 232, which are circumferentially attached to throat 206 adjacent to orifice 204. Band 228 may include a fastener 214, e.g., a hook-and-loop type fastener. String 230 may also include a fastener, e.g., fastener 234, which may be a cord lock having a release button 236. Band 228 and string 230 enable placing throat 206 and orifice 204 into a closed configuration having a conical shape. That is, string 230 may be constricted about orifice 204 more than band 228 may be constricted about throat 206 such that the diameter or width of orifice 204 is smaller than the diameter or width of throat 206. Thus, in the closed configuration (e.g., FIG. 4) the diameter or width of throat 206 may be between approximately 0.75 inches and six inches whereas the diameter or width of orifice 204 may be between approximately 0.5 inches and 5.5 inches while also being smaller than the diameter or width of throat 206 in the closed configuration. For example, in the closed configuration, the diameter of throat 206 may be approximately two inches and the diameter orifice 204 may be one inch, thus creating a tip 238 of enclosure 200 having a conical shape. Further, in the closed configuration, band 228 and string 230 provide substantial mass to tip 238, thereby providing tip 238 with the ability to resist some deformation and facilitate introduction of tip 238 through an incision.

Figure 5:
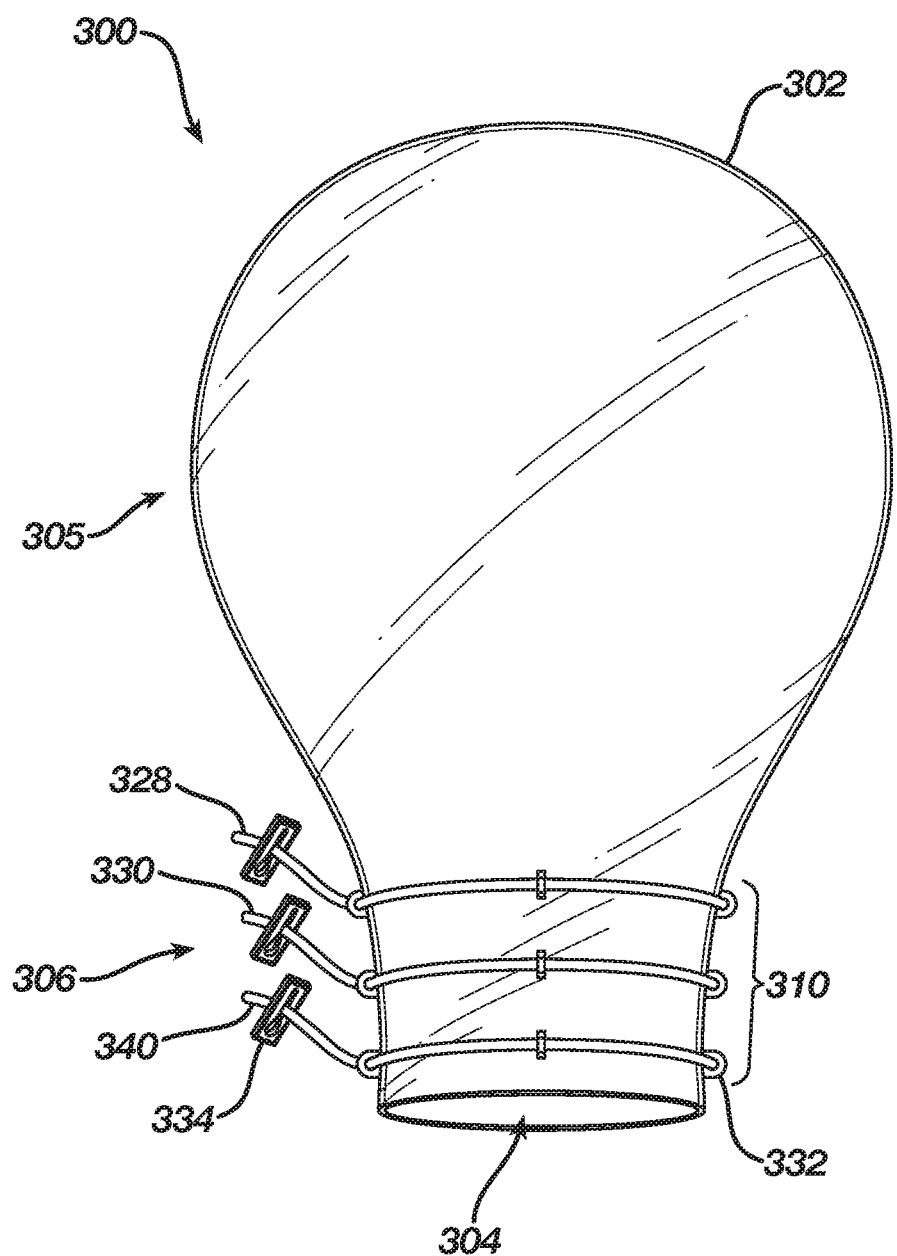
FIG. 5 depicts another a second alternative embodiment of a delivery sleeve.

As noted above, in various embodiments, the cinching mechanism may include at least a single band or string, and/or multiple bands or strings. For example, FIG. 5 reflects a delivery sleeve 300 with a cinching mechanism 310 in a loose configuration. Cinching mechanism 310 includes a first string 328, a second string 330, and a third string 340 disposed about throat 306, through eyelets 332, with string 340 disposed adjacent to orifice 304. Cinching mechanism 310, may also include a slide clamps 334 disposed on at least one of the strings, which may be used to maintain the strings in a constricted or closed configuration. String 340 may be constricted more than string 330, which may be constricted more than string 328. Accordingly, in the closed configuration, tip 340 may have a conical shape imparted by strings 328, 330, and 340. Alternatively, strings 328, 330, and 340 may be constricted by the same or approximately the same amount to impart a cylindrical shape to throat 306.

Figure 6:
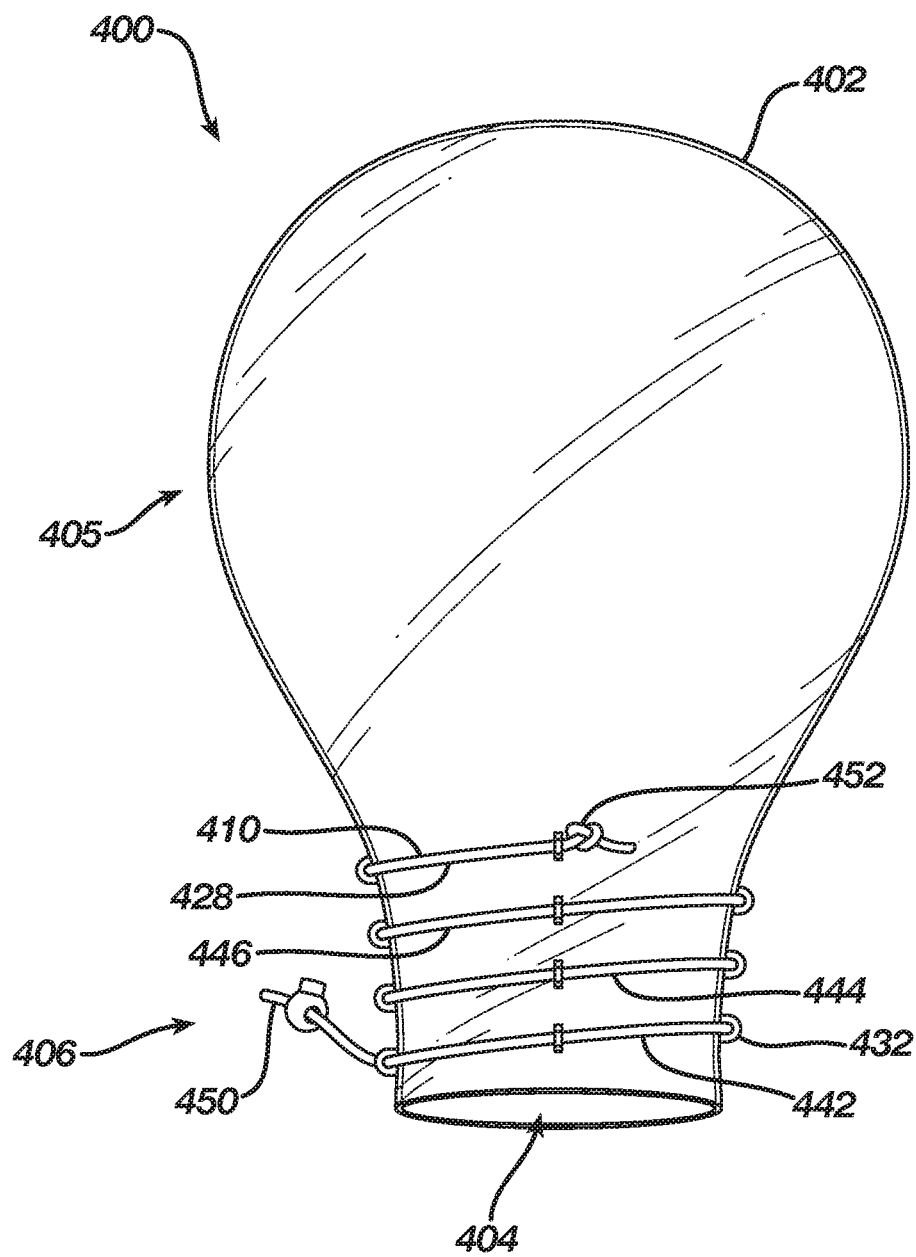
FIG. 6 depicts a third alternative embodiment of a delivery sleeve.
Figure 7:
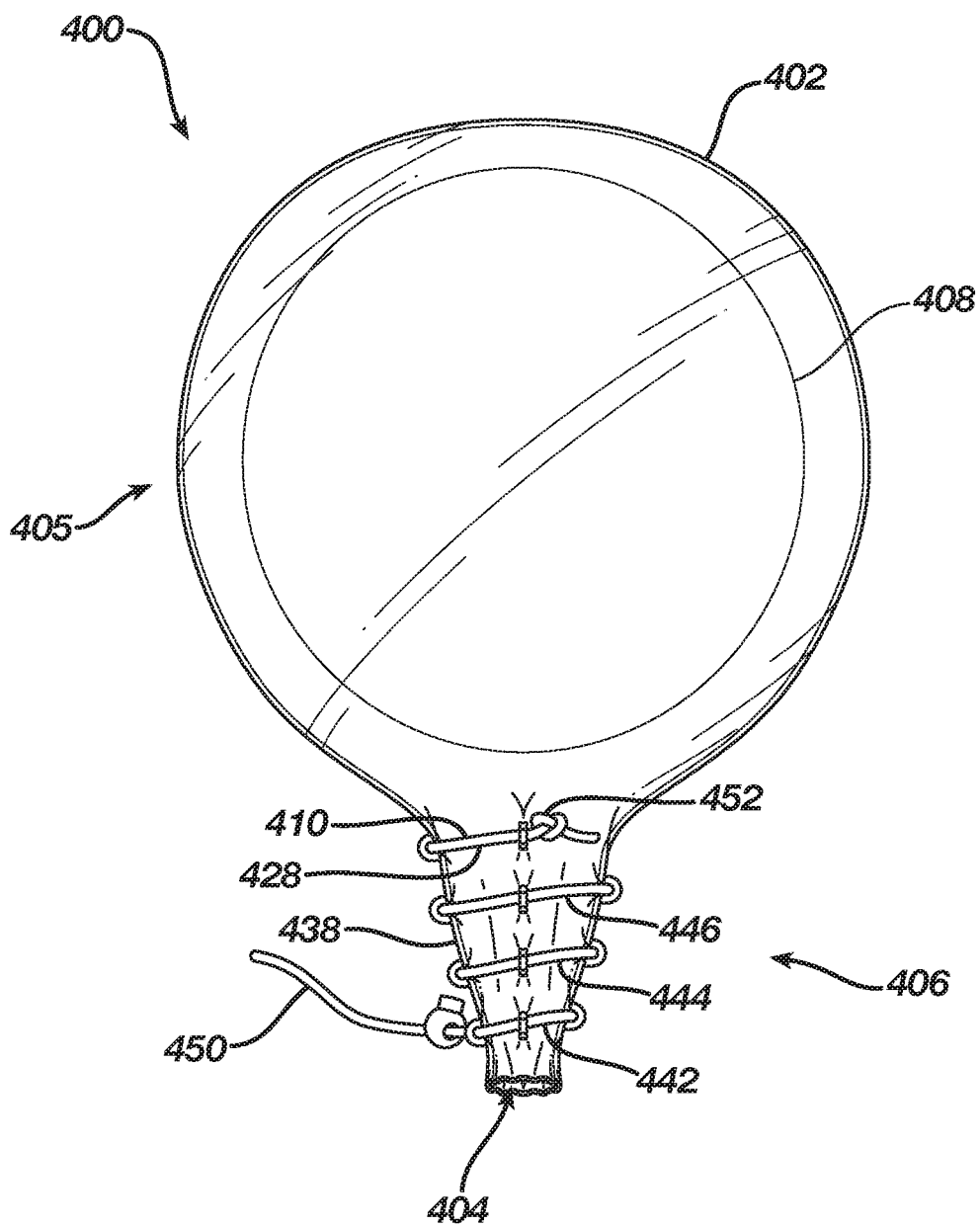
FIG. 7 depicts the delivery sleeve of FIG. 6 in a closed configuration.

FIGS. 6 and 7 reflect an alternate embodiment of a delivery sleeve. In FIG. 6, delivery sleeve 400 is shown with cinching mechanism 410 in a loose configuration. In FIG. 7 delivery sleeve 400 is shown with cinching mechanism 410 in a cinched configuration. In this embodiment, cinching mechanism 410 may include a string 428 (or a band) disposed about throat 410 though eyelets 432 along an angled or helical path. As shown, string 428 has multiple convolutions, e.g., first convolution 442, second convolution 444, and third convolution 446. At least a portion of first convolution 442 is disposed adjacent to orifice 404. First convolution 442 may further include a first end 450 of string 428. Third convolution 446 may include a second end 452 that is fixedly attached to throat 406, e.g., by ultrasonic welding, or by providing a bead or knot larger than a hole in eyelet 432 such that the bead or knot cannot pass through eyelet 432. By displacing first end 450 away from orifice 404, e.g., by pulling on it, first convolution 442 will reduce in diameter by a greater amount than second convolution 444, which will reduce in diameter by a greater amount than third convolution 446. Accordingly, tip 438 will have a conical shape when throat 206 is placed in the closed configuration shown in FIG. 7. Although this embodiment is shown as having three convolutions, it should be understood that greater or fewer convolutions would also enable placing tip 438 into a conical shape in the closed configuration. For example, even an incomplete convolution (e.g., 270 degrees) would permit for a closed configuration of throat 406 having a tip 438 with a conical shape.

In some embodiments, a lubricant can be dispersed inside the enclosure (e.g., 102) prior to implant delivery. Optionally, in some embodiments, a lubricant coating can be used on inner surface of the enclosure. Such lubricants typically comprise one or more of the following substances: saline, glycerin, hydroxyethyl cellulose, Polyethylene glycol (PEG), propylene glycol (propane-1,2-diol), and carbomer. Suitable commercially available lubricants include, e.g., HR® Lubricating Jelly and McKesson Lubricating Jelly. These lubricants can be provided into the enclosure as a liquid or fluid; or alternatively as semi-liquid or paste; or alternatively as dry powders and/or dry coatings which are activated by water. Optionally, in some embodiments, a lubricious or low-friction material can be used to form the enclosure or at least coat an inner surface of the enclosure. Such coatings can comprise low-friction hydrophilic and/or hydrophobic coatings comprised of, e.g., PTFE/fluorocarbons, hydrogels, polymethacrylates; polyvinylpyrrolidone (PVP), polyurethane, acrylic polyester, vinyl resin, silicone. Suitable lubricious coatings for medical devices are available from Surmodics, Inc. (Eden Prairie, MN) and include their Serene™ lubricious coatings.

It should be understood that any of the examples and/or embodiments described herein may include various other features in addition to or in lieu of those described above. The teachings, expressions, embodiments, examples, etc. described herein should not be viewed in isolation relative to each other. Various suitable ways in which the teachings herein may be combined should be readily apparent to those of ordinary skill in the art in view of the teachings herein.

Having shown and described exemplary embodiments of the subject matter contained herein, further adaptations of the methods and systems described herein may be accomplished by appropriate modifications without departing from the scope of the claims. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. A delivery sleeve, comprising:
   an enclosure having a bulbous portion, an orifice, and a throat disposed between the bulbous portion and the orifice;
   a tissue implant comprising a silicone gel disposed within the enclosure; and
   a cinching mechanism having a fastener,
   wherein the cinching mechanism is disposed about the throat.

2. The delivery sleeve of claim 1, wherein the tissue implant comprises a breast implant.

3. The delivery sleeve of claim 2, wherein the cinching mechanism includes a string, filament, tape, strap, band, cable tie, ribbon, or a combination thereof.

4. The delivery sleeve of claim 3, wherein the fastener includes a hook-and-loop fastener, a cord lock, a ratchet, an elastic ring, a magnetic ring, or a combination thereof.

5. The delivery sleeve of claim 4, wherein the fastener is a releasable fastener.

6. The delivery sleeve of claim 3, further comprising an eyelet disposed on the throat.

7. The delivery sleeve of claim 6, wherein a portion of the cinching mechanism is disposed through the eyelet.

8. The delivery sleeve of claim 3, wherein the cinching mechanism includes implant-size indicators thereon.

9. The delivery sleeve of claim 3, wherein the orifice is a single orifice.

10. The delivery sleeve of claim 3, further including a second orifice.

11. A method of using a delivery sleeve, comprising:
    providing a tissue implant comprising a silicone gel;
    providing the delivery sleeve, the delivery sleeve comprising,
    an enclosure having a throat with an orifice, and
    a cinching mechanism having a fastener, the cinching mechanism disposed about the throat in a loose configuration such that the throat and the orifice are in an open configuration;
    inserting the tissue implant into the enclosure through the orifice and the throat; and
    changing the configuration of the throat and orifice to a closed configuration.

12. The method of claim 11, wherein the step of changing the configuration to a closed configuration includes cinching the cinching mechanism into a cinched configuration.

13. The method of claim 12, wherein the throat has a cylindrical shape in the closed configuration.

14. The method of claim 12, wherein the throat has a conical shape in the closed configuration.

15. The method of claim 12, further comprising inserting the orifice in the closed configuration through an incision.

* * * * *